United States Patent [19]

Dwyer et al.

[11] 3,941,871
[45] Mar. 2, 1976

[54] CRYSTALLINE SILICATES AND METHOD OF PREPARING THE SAME

[75] Inventors: Francis G. Dwyer, West Chester, Pa.; Edwin E. Jenkins, Woodstown, N.J.

[73] Assignee: Mobil Oil Corporation, New York, N.Y.

[22] Filed: Nov. 2, 1973

[21] Appl. No.: 412,393

[52] U.S. Cl. ............ 423/326; 252/431 N; 252/454; 252/455 Z; 260/448 C; 423/328; 423/331; 423/332
[51] Int. Cl.[2] ................ C01B 33/20; C01B 33/24; C01B 33/28
[58] Field of Search ............ 423/326, 327, 328–330, 423/331, 332, 333; 260/429 R, 429 BQ, 429.3, 429.7, 429.9, 439 R, 448 C, 448.2; 252/431 N, 454, 455 Z

[56] References Cited
UNITED STATES PATENTS
3,506,400   4/1970   Eberly et al. ........................ 423/328
3,702,886   11/1972  Argauer et al. ..................... 423/328

OTHER PUBLICATIONS
Ueda et al., "Molecular Sieve Zeolites–I", Copyright 1971, A.C.S. pp. 135–139.
Barrer et al., "Journal of the Chemical Society", 1959, pp. 195–208.

*Primary Examiner*—Edward J. Meros
*Attorney, Agent, or Firm*—Charles A. Huggett; Raymond W. Barclay

[57] ABSTRACT

A crystalline metal organosilicate having the composition, in its anhydrous state, as follows:

$$0.9 \pm 0.2 \ [xR_2O + (1-x) M_{2/n}O]: <.005 \ Al_2O_3: >1SiO_2$$

where M is a metal, other than a metal of Group IIIA, n is the valence of said metal, R is an alkyl ammonium radical and x is a number greater than 0 but not exceeding 1, said organosilicate being characterized by a specified X-ray diffraction pattern. Said organosilicate is prepared by digesting a reaction mixture comprising $(R_4N)_2O$, sodium oxide, an oxide of a metal other than a metal of group IIIA, an oxide of silicon and water. The crystalline organosilicates are useful as adsorbents and in their catalytically active form as catalysts for organic compound conversion.

11 Claims, No Drawings

CRYSTALLINE SILICATES AND METHOD OF PREPARING THE SAME

BACKGROUND OF THE INVENTION

1. Field of the Invention

This invention relates to novel crystalline metal organosilicates and to methods for their preparation and to organic compound conversion, especially hydrocarbon conversion therewith.

2. Description of the Prior Art

Zeolitic materials, both natural and synthetic, have been known in the past to have catalytic capability for various types of hydrocarbon conversion reactions. Certain of these zeolitic materials comprising ordered porous crystalline aluminosilicates have a definite crystalline structure, as determined by X-ray diffraction, within which there are a number of small cavities which are interconnected by a number of still smaller channels. These cavities and channels are precisely uniform in size within a specific zeolitic material. Since the dimensions of these pores are such as to accept for adsorption purposes molecules of certain dimensions while rejecting those of larger dimensions, these materials have commonly been known to be "molecular sieves" and are utilized in a variety of ways to take advantage of the adsorptive properties of these compositions.

These molecular sieves include a wide variety of positive ion containing crystalline aluminosilicates, both natural and synthetic. These aluminosilicates can be described as a rigid three-dimensional network of $SiO_4$ and $AlO_4$ in which the tetrahedra are cross linked by the sharing of oxygen atoms whereby the ratio of the total aluminum and silicon atoms to oxygen is 1:2. The electrovalence of the tetrahedra containing aluminum is balanced by the inclusion in the crystal of a cation, for example an alkali metal or alkaline earth cation. Thus, a univalent positive sodium cation balances one negatively charged aluminosilicate tetrahedra where an alkaline earth metal cation is employed in the crystal structure of an aluminosilicate, it balances two negatively charged tetrahedra because of its doubly positive valence. One type of cation may be exchanged either entirely or partially by another type of cation utilizing ion exchange techniques in a conventional manner. By means of such cation exchange, it has been possible to vary the size of the pores in a given aluminosilicate by suitable selection of the particular cation. The spaces between the tetrahedra are occupied by moles of water prior to dehydration.

One such group of crystalline aluminosilicates, designated as those of the ZSM-5 type, have been known and are particularly described in U.S. Pat. No. 3,702,886, the disclosure of which is incorporated herein by reference. The ZSM-5-type crystalline aluminosilicates have been prepared, for example, from a solution containing a tetraalkyl ammonium hydroxide, sodium oxide, an oxide of aluminum or gallium, an oxide of silicon or germanium and water and have been found to be characterized by a specific X-ray diffraction pattern.

The above crystalline aluminosilicates, as previously noted, have been characterized by the presence of aluminum and silicon, the total of such atoms to oxygen being 1:2. The amount of alumina present appears directly related to acidity characteristics of the resulting product. A low alumina content has been recognized as being advantageous in attaining a low degree of acidity which in many catalytic reactions is translated into low coke making properties and low aging rates.

SUMMARY OF THE INVENTION

In accordance with the present invention, there is provided a family of crystalline metal organosilicates which are essentially free of Group IIIA metals, i.e. aluminum and/or gallium. These organosilicates have surprisingly been found to be characterized by an X-ray diffraction pattern characteristic of the above-noted ZSM-5-type crystalline aluminosilicates. In addition to having such characteristic X-ray diffraction pattern, the crystalline organosilicates of the present invention can be identified in their anhydrous state in terms of mole ratios of oxides as follows:

$$0.9 \pm 0.2\ [xR_2O + (1-x)\ M_{2/n}O]: < .005\ Al_2O_3:>1\text{-}SiO_2$$

where M is a metal other than a metal of Group IIIA, $n$ is the valence of said metal, R is an alkyl ammonium radical and x is greater than O but not exceeding 1. Preferably R is a tetraalkyl ammonium radical, the alkyl groups of which contain 2–5 carbon atoms.

In the above composition, $R_2O$ and $M_{2/n}O$ may be removed by replacement with or conversion to other desired components which serve to enhance catalytic activity, stability and/or adsorption characteristics. It is particularly contemplated that R and/or M may be at least partially in the ammonium form as a result of ion exchange.

As above noted, the family of crystalline metal organosilicates disclosed and claimed herein have a definite X-ray diffraction pattern. Such X-ray diffraction pattern, similar to that for the ZSM-5 zeolites, shows the following significant lines:

TABLE 1

| Interplanar spacing d(A): | | Relative intensity |
|---|---|---|
| 11.1 | ± 0.2 | s |
| 10.0 | ± 0.2 | s |
| 7.4 | ± 0.15 | w |
| 7.1 | ± 0.15 | w |
| 6.3 | ± 0.1 | w |
| 6.04 | ⎫ | |
| 5.97 | ⎬ ± 0.1 | w |
| 5.56 | ± 0.1 | w |
| 5.01 | ± 0.1 | w |
| 4.60 | ± 0.08 | w |
| 4.25 | ± 0.08 | w |
| 3.85 | ± 0.07 | vs |
| 3.71 | ± 0.05 | s |
| 3.04 | ± 0.03 | w |
| 2.99 | ± 0.02 | w |
| 2.94 | ± 0.02 | w |

These values were determined by standard techniques. The radiation was the K-alpha doublet of copper and a Geiger Counter Spectrometer with a strip chart pen recorder was used. The peak heights, I, and the positions as a function of two times theta, where theta is the Bragg angle, were read from the spectrometer chart. From these, the relative intensities, 100 $I/I_0$, where $I_0$ is the intensity of the strongest line or peak and d(obs.), the interplanar spacing in A, corresponding to the recorded lines were calculated. In Table I the relative intensities are given in terms of the symbols s = strong, w = weak and vs = very strong.

The crystalline metal organosilicate of the present invention can be used either in the alkali metal form, e.g. the sodium form, other desired metal form, the ammonium form or the hydrogen form. Preferably, one or other of the last two forms is employed. They can also be used in intimate combination with a hydrogenation component such as tungsten, vanadium, molybdenum, rhenium, nickel, cobalt, chromium, manganese or a noble metal such as platinum or palladium where a hydrogenation-dehydrogenation function is to be performed. Such component can suitably be impregnated on or physically intimately admixed with the crystalline organosilicate.

The above organosilicates as synthesized or after impregnation can be beneficially converted to another form by thermal treatment. This can be done by heating to a temperature in the range of 200° to 600°C. in an atmosphere such as air, nitrogen, etc. and that atmospheric or subatmosphereic pressures for between 1 and 48 hours. Dehydration may also be performed at lower temperatures merely by placing the organosilicate in a vacuum, but a longer time is required to obtain a sufficient amount of dehydration.

The crystalline metal organosilicates of the invention can be suitably synthesized by preparing a solution containing $(R_4N)_2O$, sodium oxide, an oxide of a metal other than a metal of Group IIIA and water and having a composition in terms of mole ratios of oxides falling within the following ranges:

TABLE II

|  | Broad | Preferred |
|---|---|---|
| $OH^-/SiO_2$ | .01–5 | .05–1.0 |
| $R_4N^+/(R_4N^+ + Na^+)$ | .05–1.0 | .1–.8 |
| $H_2O/OH^-$ | 50–1000 | 50–500 |
| $SiO_2/M_{2/n}O$ | >1 | >3 | wherein R is an alkyl radical, preferably between 2 and 5 carbon atoms and M is total metal. Thereafter, the mixture is maintained until crystals of the metal organosilicate are formed. Preferably, crystallization is performed under pressure in an autoclave or static bomb reactor. The temperature ranges from 100°C. to 200°C. generally, but at lower temperatures, e.g. about 100°C., crystallization time is longer. Thereafter, the crystals are separated from the liquid and recovered. Typical reaction conditions consist of heating the foregoing reaction mixture to a temperature from about 100°C. to 175°C. for a period of time of from about 6 hours to 60 days. The more preferred temperature range is from about 100°C. to 175°C. with the amount of time at a temperature in such range being from about 12 hours to 30 days.

The treatment of the amorphous mixture is carried out until crystals form. The resulting crystalline product is separated from the reaction medium, as by cooling to room temperature, filtering and water washing. The product so obtained is dried, e.g. at 230°F., for from about 8 to 24 hours. If desired, milder conditions may be employed, e.g. room temperature under vacuum.

The desired crystalline organosilicate can be prepared utilizing materials which supply the appropriate oxide. Such compositions include sodium silicate, colloidal silica, silica hydrosol, silica gel, silicic acid, sodium hydroxide, compounds of the desired metal, other than a metal of Group IIIA and tetraalkylammonium compounds, e.g. tetrapropylammonium bromide. In addition to tetrapropylammonium compounds, it is contemplated that tetramethyl, tetraethyl or tetrabutyl ammonium compounds may similarly be employed. It will be understood that each oxide component utilized in the reaction mixture for preparing the crystalline metal organosilicates of this invention can be supplied by one or more initial reactants and they can be mixed together in any order. For example, sodium oxide can be supplied by an aqueous solution of sodium hydroxide or by an aqueous solution of sodium silicate; tetrapropylammonium can be supplied in the form of its hydroxide as can the other tetraalkylammonium radicals noted hereinabove. The reaction mixture can be prepared either batchwise or continuously. Crystal size and crystallization time of the crystalline metal organosilicate composition will vary with the nature of the reaction mixture employed.

The crystalline organosilicates described herein are substantially free of alumina, but may contain very minor amounts of such oxide attributable primarily to the presence of aluminum impurities in the reactants and/or equipment employed. Thus, the molar ratio of alumina to silica will be in the range of 0 to less than 0.005 $Al_2O_3$ to more than 1 mole of $SiO_2$. Generally, the latter may range from >1 $SiO_2$ up to 500 or more.

DESCRIPTION OF SPECIFIC EMBODIMENTS

The crystalline metal organosilicates as synthesized can have the original components thereof replaced by a wide variety of others according to techniques well known in the art. Typical replacing components would include hydrogen, ammonium, alkyl ammonium and aryl ammonium and metals, other than metals of Group IIIA, including mixtures of the same. The hydrogen form may be prepared, for example, by substitution of original sodium with ammonium. The composition is then calcined at a temperature of, say, 1000°F. causing evolution of ammonia and retention of hydrogen in the composition. Of the replacing metals, preference is accorded to metals of Groups II, IV and VIII of the Periodic Table.

The crystalline silicates are then preferably washed with water and dried at a temperature ranging from 150°F. to about 600°F. and thereafter calcined in air or other inert gas at temperatures ranging from 500°F. to 1500°F. for periods of time ranging from 1 to 48 hours or more.

Regardless of the synthesized form of the organosilicate the spatial arrangement of atoms which form the basic crystal latices remain essentially unchanged by the described replacement of sodium or other alkali metal or by the presence in the initial reaction mixture of metals in addition to sodium, as determined by an X-ray powder diffraction pattern of the resulting organosilicate. The X-ray diffraction patterns of such products are essentially the same as those set forth in Table I above.

The crystalline silicates prepared in accordance with the instant invention are formed in a wide variety of particular sizes. Generally, the particles can be in the form of powder, a granule, or a molded product such as an extrudate having a particle size sufficient to pass through a 2 mesh (Tyler) screen and be maintained on a 400 mesh (Tyler) screen in cases where the catalyst is molded such as by extrusion. The aluminosilicate can be extruded before drying or dried or partially dried and then extruded.

In the case of many catalysts, it is desired to incorporate the new crystalline silicate with another material resistant to the temperatures and other conditions employed in organic processes. Such materials include active and inactive materials and synthetic and naturally occurring zeolites as well as inorganic materials such as clays, silica and/or metal oxides. The latter may be either naturally occurring or in the form of gelatinous precipitates or gels including mixtures of silica and metal oxides. Use of the material in conjunction with the new crystalline aluminosilicate, i.e. combined therewith which is active, tends to improve the conversion and/or selectivity of the catalyst in certain organic conversion processes. Inactive materials suitably serve as diluents to control the amount of conversion in a given process so that products can be obtained economically and in an orderly manner without employing other means for controlling the rate of reaction. Normally, crystalline materials have been incorporated into naturally occurring clays, e.g. bentonite and kaolin to improve the crush strength of the catalyst under commercial operating conditions. These materials, i.e. clays, oxides etc., function as binders for the catalyst. It is desirable to provide a catalyst having good crush strength because in a petroleum refinery the catalyst is often subjected to rough handling which tends to break the catalyst down into powder-like materials which cause problems in processing. These clay binders have been employed for the purpose of improving the crush strength of the catalyst.

Naturally occurring clays that can be composited with the crystalline metal organosilicate described herein include the montmorillonite and kaolin family, which families include the sub-bentonites and the kaolins known commonly as Dixie, McNamee, Georgia and Florida or others in which the main constituent is halloysite, kaolinite, dickite, nacrite or anauxite. Such clays can be used in the raw state as originally mined or initially subjected to calcination, acid treatment or chemical modification.

In addition to the foregoing materials, the crystalline metal organosilicate may be composited with a porous matrix material such as silica-alumina, silica-magnesia, silica-zirconia, silica-thoria, silica-berylia, silica-titania as well as ternary compositins such as silica-alumina-thoria, silica-alumina-zirconia, silica-alumina-magnesia and silica-magnesia-zirconia. The matrix can be in the form of a cogel. The relative proportions of finally divided crystalline metal organosilicate and inorganic oxide gel matrix can vary widely with the crystalline organosilicate content ranging from about 1 to 90 percent by weight and more usually in the range of about 2 to about 50 percent by weight of the composite.

Employing the catalyst of this invention, containing a hydrogenation component, heavy petroleum residual stocks, cycle stocks, and other hydrocrackable charge stocks can be hydrocracked at temperatures between 400°F. and 825°F. using molar ratios of hydrogen to hydrocarbon charge in the range between 2 and 80. The pressure employed will vary between 10 and 2,500 psig and the liquid hourly space velocity between 0.1 and 10.

Employing the catalyst of this invention for catalytic cracking, hydrocarbon cracking stocks can be cracked at a liquid hourly space velocity between about 0.5 and 50, a temperature between about 550°F. and 1100°F., a pressure between about subatmospheric and several hundred atmospheres.

Employing a catalytically active form of a member of the family of zeolites of this invention containing a hydrogenation component, reforming stocks can be reformed employing a temperature between 700°F. and 1000°F. The pressure can be between 100 and 1000 psig, but is preferably between 200 and 700 psig. The liquid hourly space velocity is generally between 0.1 and 10, preferably between 0.5 and 4 and the hydrogen to hydrocarbon mole ratio is generally between 1 and 20, preferably between 4 and 12.

The catalyst can also be used for hydroisomerization of normal paraffins when provided with a hydrogenation component, e.g. platinum. Hydroisomerization is carried out at a temperature between 200° and 700°F., preferably 300° to 550°F., with a liquid hourly space velocity between 0.01 and 2, preferably between 0.25 and 0.50 employing hydrogen such that the hydrogen to hydrocarbon mole ratio is between 1:1 and 5:1. Additionally, the catalyst can be used for olefin isomerization employing temperatures between 30°F. and 500°F.

In order to more fully illustrate the nature of the invention and a manner of practicing the same, the following examples are presented.

In the examples which follow, whenever adsorption data are set forth, it was determined as follows:

A weighed sample of the material was contacted with the desired pure adsorbate vapor in an adsorption chamber at a pressure less than the vapor-liquid equilibrium pressure of the adsorbate at room temperature. This pressure was kept constant during the adsorption period which did not exceed about eight hours. Adsorption was complete when a constant pressure in the adsorption chamber was reached, i.e. 12 mm. of mercury for water and 20 mm. for n-hexane and cyclohexane. The increase in weight was calculated as the adsorption capacity of the sample.

EXAMPLE 1

A crystalline organosilicate containing tin and sodium was synthesized from tetrapropylammonium bromide, colloidal silica, stannous chloride and sodium hydroxide. A mixture of 19.1 grams of colloidal silica (30 weight percent $SiO_2$), 15.6 grams of tetrapropylammonium bromide, 1.5 grams of NaOH, 1.0 gram of $SnCl_4 \cdot 5H_2O$ and 100 grams of water was prepared. This mixture was placed in an autoclave and maintained for 22 hours at 300°F. and autogenous pressure. The product was removed, filtered, water washed and dried at 230°F. X-ray diffraction analysis established the product as being crystalline and having the X-ray diffraction pattern set forth in Table I.

The reaction composition and product analysis are shown below:

| Reaction Composition | Moles |
|---|---|
| $SiO_2$ | .095 |
| $[(C_3H_8)_4N]_2O$ | .0294 |
| $H_2O$ | 6.3 |
| $Na_2O$ | .01875 |
| $SnO_2$ | .0029 |
| $R_4N/R_4N + Na$ | .610 |
| $OH^-/SiO_2$ | .395 |
| $H_2O/OH^-$ | 168.3 |
| $SiO_2/M_{2/n}O$ | 4.38 | where R is propyl and M is total metal.

| Product Composition | Wt. Percent |
|---|---|
| $Al_2O_3$ | 0.06 |
| Na | 3.1 |
| $SiO_2$ | 91 (approx.) |
| Sn | 6.1 |

EXAMPLE 2

A crystalline organosilicate containing sodium was produced from tetrapropylammonium bromide, colloidal silica and sodium hydroxide. A mixture of 19.1 grams of colloidal silica (30 weight percent $SiO_2$), 15.6 grams tetrapropylammonium bromide, 1.0 gram NaOH and 100 grams of water was prepared. This mixture was placed in an autoclave and maintained for 24 hours at 300°F. and autogenous pressure. The product was removed, filtered, water washed and dried at 230°F. X-ray diffraction analysis established the product as being crystalline and having the X-ray diffraction pattern set forth in Table I.

The reaction composition and product analysis are shown below:

| Reaction Composition | Moles |
|---|---|
| $SiO_2$ | .095 |
| $[(C_3H_8)_4N]_2O$ | .0294 |
| $H_2O$ | 6.3 |
| $Na_2O$ | .0125 |
| $R_4N/R_4N + Na$ | .701 |
| $OH^-/SiO_2$ | .263 |
| $H_2O/OH^-$ | 252.5 |
| $SiO_2/Na_2O$ | 7.6 |
| Product Composition | Wt. Percent |
| $Al_2O_3$ | 0.13 |
| N | 0.69 |
| Na | 0.80 |
| $SiO_2$ | 98.8 |
| Adsorption | Wt. Percent |
| Cyclohexane | 2.4 |
| Water | 4.6 |

EXAMPLE 3

A crystalline organosilicate containing sodium was synthesized from sodium silicate, sodium hydroxide, sulfuric acid and tetrapropylammonium bromide. A mixture of 40 grams of sodium silicate "Q" Brand ($Na_2O/SiO_2$=0.299), 31.2 grams of tetrapropylammonium bromide, 0.5 gram NaOH, 4.6 grams $H_2SO_4$ and 200 grams of water was prepared. This mixture was maintained for 6 days at 212°F. and atmospheric pressure. The product was removed, filtered, water washed and dried at about 250°F. X-ray diffraction analysis established the product as being crystalline and having the X-ray diffraction pattern set forth in Table I.

The reaction composition is shown below:

| Reaction Composition | Moles |
|---|---|
| $SiO_2$ | .1896 |
| $[(C_3H_8)_4N]_2O$ | .0587 |
| $H_2O$ | 12.5 |
| $Na_2O$ | .0943 |
| $R_4N/R_4N + Na$ | .384 |
| $OH^-/SiO_2$ | .499 |
| $H_2O/OH^-$ | 132.1 |
| $SiO_2/Na_2O$ | 2.01 |

After calcination for 16 hours at 1000°F. in air, the product was used to effect selective separation of $C_8$ aromatic isomers. As will be evident from the data shown below in Table III, ortho xylene and meta xylene are both very selectively excluded at 200°C., while para xylene and ethylbenzene are both sorbed.

TABLE III

| A. Pure Components | Retention Time, Sec. |
|---|---|
| Mesitylene | 10 |
| o-Xylene | 11 |
| m-Xylene | 11 |
| p-Xylene | 394 |
| Ethylbenzene | 319 |
| B. $C_8$-Aromatic Mixture | |
| Major Separation | No Resolution |
| Minor Separation | OX, MX/PX, EB |
| Number of Peaks | 2 |
| Resolution | Excellent |
| Capacity ($\mu$ l/g) | 111 |

EXAMPLE 4

A crystalline organosilicate containing sodium was synthesized from sodium silicate, sulfuric acid, tetrapropylammonium bromide and water. A mixture of 80 grams of sodium silicate ($Na_2O/SiO_2 = 0.299$), 8 grams of sulfuric acid, 60 grams of tetrapropylammonium bromide and 200 grams of water was prepared. This mixture was maintained at 212°F. for 66 hours and autogenous pressure. The product was removed, filtered, water washed and dried at about 250°F. X-ray diffraction analysis established the product as being crystalline and having the X-ray diffraction pattern set forth in Table I.

The reaction composition and product analysis are shown below:

| Reaction Composition | Moles |
|---|---|
| $SiO_2$ | .379 |
| $[(C_3H_8)_4N]_2O$ | .113 |
| $H_2O$ | 13.9 |
| $Na_2O$ | .176 |
| $R_4N/R_4N + Na$ | .391 |
| $OH^-/SiO_2$ | .498 |
| $H_2O/OH^-$ | 73.66 |
| $SiO_2/Na_2O$ | 2.15 |
| Product Composition | Wt. Percent |
| $Al_2O_3$ | 0.18 |
| N | 0.78 |
| Na | 1.3 |
| $SiO_2$ | 97 (approx.) |

EXAMPLE 5

A crystalline organosilicate containing sodium was synthesized from sodium silicate, sulfuric acid, sodium hydroxide, tetramethylammonium chloride, tetrapropylammonium bromide and water. A mixture of 40 grams of sodium silicate ($Na_2O/SiO_2 = 0.299$), 1.5 grams of sodium hydroxide, 3 grams of sulfuric acid, 6 grams of tetramethylammonium chloride, 6 grams of tetrapropylammonium bromide and 231 grams of water was prepared. This mixture was maintained for 113 hours at 320°F. and autogenous pressure. The product was removed, filtered, water washed and dried at about 250°F. X-ray diffraction analysis showed the crystalline material to have the X-ray diffraction pattern set forth in Table I.

The reaction composition is shown below:

| Reaction Composition | Moles |
|---|---|
| $SiO_2$ | .1897 |
| $[(C_3H_8)_4N]_2O$ | .0113 |
| $[(CH_3)_4N]_2O$ | .0274 |
| $H_2O$ | 14.2 |
| $Na_2O$ | .0755 |
| $R_4N/R_4N + Na$ | .339 |
| $OH^-/SiO_2$ | .473 |
| $H_2O/OH^-$ | 158.1 |
| $SiO_2/Na_2O$ | 2.513 | where R is propyl + methyl.

EXAMPLE 6

A crystalline organosilicate containing sodium was synthesized from sodium silicate, sodium hydroxide, sulfuric acid, tetrapropylammonium bromide and water. A mixture of 160 grams of sodium silicate ($Na_2O/SiO_2 = 0.299$), 2 grams of sodium hydroxide, 18.4 grams of sulfuric acid, 124.8 grams of tetrapropylammonium bromide and 800 grams of water was prepared. This mixture was maintained for 40 hours at 212°F. and autogenous pressure. The product was removed, filtered, water washed and dried at about 250°F. X-ray diffraction analysis showed the crystalline material to have the X-ray diffraction analysis set forth in Table I.

The reaction composition and product analysis are shown below:

| Reaction Composition | Moles |
|---|---|
| $SiO_2$ | .759 |
| $[(C_3H_8)_4N]_2O$ | .2347 |
| $H_2O$ | 50.02 |
| $Na_2O$ | .2521 |
| $R_4N/R_4N + Na$ | .482 |
| $OH^-/SiO_2$ | .1696 |
| $H_2O/OH^-$ | 388.7 |
| $SiO_2/Na_2O$ | 3.01 |
| Product Composition | Wt. Percent |
| $Al_2O_3$ | 0.202 |
| Na | 1.5 |
| $SiO_2$ | 96.5 |

EXAMPLE 7

A crystalline organosilicate containing zirconium and sodium was synthesized from colloidal silica, sodium hydroxide, zirconium oxide (25 percent solution), tetrapropylammonium bromide and water. A mixture of 50 grams of colloidal silica (30 weight percent $SiO_2$), 1 gram of sodium hydroxide, 25 grams of zirconium oxide (25 percent solution), 20 grams of tetrapropylammonium bromide and 50 grams of water was prepared. This mixture was maintained for 25 days at 300°F. and autogenous pressure. The product was removed, filtered, water washed and dried at about 250°F. X-ray diffraction analysis showed the crystalline material to have the X-ray diffraction pattern in Table I.

The reaction composition and product analysis are shown below:

| Reaction Composition | Moles |
|---|---|
| $SiO_2$ | .2496 |
| $[(C_3H_8)_4N]_2O$ | .0376 |
| $H_2O$ | 5.76 |
| $Na_2O$ | .0125 |
| $ZrO_2$ | .0507 |
| $R_4N/R_4N + Na$ | .750 |
| $H_2O/OH^-$ | 230.4 |
| $SiO_2/M_{2/n}O$ | 3.94 |
| Product Composition | Wt. Percent |
| $Al_2O_3$ | <0.04 |
| N | 0.52 |
| Na | 0.24 |

EXAMPLE 8

A crystalline organosilicate containing calcium and sodium was synthesized from colloidal silica, sodium hydroxide, calcium hydroxide, tetrapropylammonium bromide and water. A mixture of 50 grams of colloidal silica (30 weight percent of $SiO_2$), 1 gram NaOH, 1 gram $Ca(OH)_2$, 20 grams of tetrapropylammonium bromide and 100 grams of water was prepared. The mixture was maintained for 16 days at 212°F. and autogenous pressure. The product was removed, filtered, water washed and dried at about 250°F. X-ray analysis showed the crystalline material to have the X-ray diffraction pattern set forth in Table I.

Reaction composition and product analysis are shown below:

| Reaction Composition | Moles |
|---|---|
| $SiO_2$ | .2496 |
| $[(C_3H_8)_4N]_2O$ | .0376 |
| $H_2O$ | 7.50 |
| $Na_2O$ | .0125 |
| CaO | .0135 |
| $R_4N/R_4N + Na$ | .750 |
| $OH^-/SiO_2$ | .100 |
| $H_2O/OH^-$ | 300 |
| $SiO_2/M_{2/n}O$ | 9.6 |
| Product Composition | Wt. Percent |
| $Al_2O_3$ | <0.04 |
| N | 0.63 |
| Na | 0.66 |
| $SiO_2$ | 96 (approx.) |
| Ca | 2.9 |

EXAMPLE 9

A crystalline organosilicate containing nickel and sodium was synthesized from colloidal silica, sodium hydroxide, nickel nitrate, tetrapropylammonium bromide and water. A mixture of 50 grams of colloidal silica (30 weight percent $SiO_2$), 1.5 grams of NaOH, 4 grams of $Ni(NO_3)_2 \cdot 6H_2O$, 20 grams of tetrapropylammonium bromide and 60 grams of water was prepared. This mixture was maintained for 19 days at 212°F. and autogenous pressure. The product was removed, filtered, water washed and dried at about 250°F. X-ray diffraction analysis showed the crystalline material to have the X-ray diffraction pattern set forth in Table I. The reaction composition and product analysis are shown below:

| Reaction Composition | Moles |
|---|---|
| $SiO_2$ | .2496 |
| $[(C_3H_8)_4N]_2O$ | .0376 |
| $H_2O$ | 5.36 |
| $Na_2O$ | .0188 |
| NiO | .01376 |
| $R_4N/R_4N + Na$ | .667 |
| $OH^-/SiO_2$ | .150 |
| $H_2O/OH^-$ | 142.9 |
| $SiO_2/M_{2/n}O$ | 7.68 |

-continued

| Product Composition | Wt. Percent |
|---|---|
| $Al_2O_3$ | <0.04 |
| N | 0.65 |
| Na | 0.71 |
| $SiO_2$ | 92 (approx.) |
| Ni | 7.0 |

EXAMPLE 10

A crystalline organosilicate containing zinc and sodium was synthesized from colloidal silica, sodium hydroxide, zinc nitrate, tetrapropylammonium bromide and water. A mixture of 100 grams of colloidal silica, 4 grams NaOH, 4 grams of $Zn(NO_3)_2 \cdot 6H_2O$, 25 grams of tetrapropylammonium bromide and 100 grams of water was prepared. This mixture was maintained for 14 days at 212°F. and autogenous pressure. The product was removed, filtered, water washed, and dried at about 250°F. X-ray diffraction analysis showed the crystalline material to have the X-ray diffraction pattern set forth in Table I.

The reaction composition and product analysis are shown below:

| Reaction Composition | Moles |
|---|---|
| $SiO_2$ | .4992 |
| $[(C_3H_8)_4N]_2O$ | .047 |
| $H_2O$ | 9.53 |
| $Na_2O$ | .05 |
| ZnO | .0059 |
| $R_4N/R_4N + Na$ | .485 |
| $OH^-/SiO_2$ | .200 |
| $H_2O/OH^-$ | 95.3 |
| $SiO_2/M_{2/n}O$ | 8.93 |
| Product Composition | Wt. Percent |
| $Al_2O_3$ | <0.04 |
| N | 0.69 |
| Na | 1.3 |
| $SiO_2$ | 95 (approx.) |
| ZnO | 2.63 |

We claim:

1. A crystal metal organosilicate having a composition, in its anhydrous state, in terms of mole ratios of oxides as follows:

$$0.9 \pm 0.2 \ [xR_2O + (1-x) M_{2/n}O] : < .005 \ Al_2O_3 : > 1SiO_2$$

where M is sodium or sodium in combination with tin, calcium, nickel or zinc, R is a tetraalkylammonium and x is a number greater than 0 but not exceeding 1, said organosilicate having the X-ray diffraction lines set forth in Table I of the specification.

2. A crystalline silicate resulting from thermal treatment of the composition of claim 1 by heating to a temperature in the range of 200° to 600°C. for between 1 and 48 hours.

3. The composition of claim 1 which has been exchanged with ammonium ions.

4. The composition of claim 1 wherein R is tetrapropylammonium.

5. The composition of claim 1 wherein M comprises tin.

6. The composition of claim 1 wherein M comprises sodium.

7. The composition of claim 1 wherein M comprises calcium.

8. The composition of claim 1 wherein M comprises nickel.

9. The composition of claim 1 wherein M comprises zinc.

10. A method of preparing a crystalline metal organosilicate as defined in claim 1 which comprises preparing a mixture containing a tetraalkylammonium compound, sodium oxide, an oxide of tin, calcium, nickel, or zinc, an oxide of silicon and water and having a composition in terms of mole ratios of oxides falling within the following ranges:

| | |
|---|---|
| $OH^-/SiO_2$ | .01 – 5 |
| $R_4N^+/(R_4N^+ + Na^+)$ | .05 – 1.0 |
| $H_2O/OH^-$ | 50 – 1000 |
| $SiO_2/M_{2/n}O$ | >1 | wherein R is alkyl radical and M is total metal, maintaining the mixture at a temperature at about 100°C. to about 175°C. until crystals of said metal organosilicate are formed and separated and recovering said crystals.

11. A method of preparing a crystalline metal organosilicate as defined in claim 1 which comprises preparing a mixture containing a tetraalkylammonium compound, sodium oxide, an oxide of tin, calcium, nickel or zinc, an oxide of silicon and water and having a composition in terms of mole ratios of oxides falling within the following ranges:

| | |
|---|---|
| $OH^-/SiO_2$ | .05 – 1.0 |
| $R_4N^+/(R_4N^+ + Na^+)$ | .1 – .8 |
| $H_2O/OH^-$ | 50 – 500 |
| $SiO_2/M_{2/n}O$ | >3 | wherein R is an alkyl radical and M is total metal, maintaining the mixture at a temperature at about 100°C. to about 175°C. until crystals of said metal organosilicate are formed and thereafter separating and recovering said crystals.

* * * * *